United States Patent
Morales

(10) Patent No.: US 8,110,144 B2
(45) Date of Patent: Feb. 7, 2012

(54) PROCESS FOR STERILIZATION OF AND CYANOACRYLATE ADHESIVES COMPOSITIONS AND DEVICES

(75) Inventor: Carlos R. Morales, Cumming, GA (US)

(73) Assignee: Chemence Medical, Inc., Alpharetta, GA (US)

( * ) Notice: Subject to any disclaimer, the term of this patent is extended or adjusted under 35 U.S.C. 154(b) by 166 days.

(21) Appl. No.: 10/944,635

(22) Filed: Sep. 17, 2004

(65) Prior Publication Data

US 2006/0062687 A1    Mar. 23, 2006

(51) Int. Cl.
*A61L 2/00*    (2006.01)
*G01N 31/00*    (2006.01)

(52) U.S. Cl. .................................. 422/1; 436/1
(58) Field of Classification Search ........... 436/1; 422/1
See application file for complete search history.

(56) References Cited

U.S. PATENT DOCUMENTS

| | | | | |
|---|---|---|---|---|
| 2,721,858 | A | 10/1955 | Joyner et al. | 260/67 |
| 2,816,093 | A | 12/1957 | Coover | 260/78.5 |
| 3,178,379 | A | 4/1965 | Wicker et al. | 260/17 |
| 3,360,124 | A | 12/1967 | Stonehill | 206/84 |
| 3,527,841 | A | 9/1970 | Overhults | 260/42.16 |
| 4,038,345 | A * | 7/1977 | O'Sullivan et al. | 525/284 |
| 4,291,122 | A * | 9/1981 | Orelski | 435/31 |
| 5,530,037 | A | 6/1996 | McDonnell et al. | 522/79 |
| 5,744,094 | A * | 4/1998 | Castberg et al. | 422/24 |
| 5,770,393 | A * | 6/1998 | Dalmasso et al. | 435/31 |
| 5,795,730 | A | 8/1998 | Tautvydas | 435/31 |
| 5,874,044 | A | 2/1999 | Kotzev | 422/40 |
| 5,922,592 | A | 7/1999 | Tautvydas | 435/287 |
| 5,928,611 | A | 7/1999 | Leung | 422/131 |
| 6,096,533 | A | 8/2000 | Tautvydas | 435/287 |
| 6,136,326 | A | 10/2000 | Kotzev | 422/400 |
| 6,248,800 | B1 | 6/2001 | Greff et al. | 521/71 |
| 6,310,166 | B1 | 10/2001 | Hickey et al. | 526/348 |
| 6,433,096 | B1 | 8/2002 | Hickey et al. | 525/244 |
| 6,451,254 | B1 * | 9/2002 | Wang et al. | 422/33 |
| 6,512,023 | B1 * | 1/2003 | Malofsky et al. | 523/111 |
| 6,579,916 | B1 | 6/2003 | Askill et al. | 522/152 |
| 6,743,858 | B2 | 6/2004 | Hickey et al. | 525/54 |
| 2002/0065336 | A1 | 5/2002 | Hickey et al. | 522/152 |
| 2002/0156203 | A1 | 10/2002 | Hickey et al. | 525/503 |
| 2003/0157588 | A1 * | 8/2003 | Matner et al. | 435/31 |
| 2003/0228273 | A1 * | 12/2003 | Greff | 424/78.35 |
| 2004/0120849 | A1 | 6/2004 | Stewart et al. | 422/22 |

FOREIGN PATENT DOCUMENTS

| | | |
|---|---|---|
| EP | 433053 A1 | 6/1991 |
| EP | 659441 B1 | 6/1995 |
| EP | 1115279 A1 | 3/2000 |
| EP | 1206291 A1 | 2/2001 |
| EP | 1345972 A2 | 7/2002 |
| WO | WO 95/21936 | 8/1995 |
| WO | WO 97/05274 | 2/1997 |

* cited by examiner

*Primary Examiner* — Kevin Joyner
(74) *Attorney, Agent, or Firm* — Jonathan Rigdon Smith, PC; Jonathan R. Smith

(57) ABSTRACT

Disclosed are processes for sterilization of cyanoacrylate adhesive compositions, the compositions, comprising 2-cyanoacrylate ester monomers, so produced and a method for assaying the effectiveness of the sterilization process. The process comprises heating the adhesive composition to from about 70° C. to about 140° C. for an effective amount of time. The effectiveness of the process can be assayed by disposing bacterial spores in the cyanoacrylate monomer, exposing the composition to a dry heat sterilization process, transferring the cyanoacrylate composition to a sterile aldose solution, transferring and exposing the sample to a nutrient medium which supports germination and growth of viable spores, incubating the samples, and determining the presence or absence of growth.

22 Claims, No Drawings

PROCESS FOR STERILIZATION OF AND CYANOACRYLATE ADHESIVES COMPOSITIONS AND DEVICES

BACKGROUND OF THE INVENTION

1. Field of the Invention

The invention relates to compositions of cyanoacrylate monomer and polymer adhesive compositions, a process for sterilizing them for application in the medical and veterinary fields, and a method of assaying the sterilization of cyanoacrylate compositions.

2. Background

It is known to use 2-cyanoacrylate esters as adhesives for bonding tissue in medical or surgical procedures performed upon the human or animal body. 2-cyanoacrylate esters polymerize rapidly, and often instantaneously, upon contact with tissue or body fluid. In these applications, the adhesive composition can be used to close wounds, as well as for covering and protecting surface injuries such as lacerations, abrasions, burns, sores and other open surface wounds. To be used in medical and veterinary fields, 2-cyanoacrylates must be sterilized. This is generally done in sealed containers to provide sterility, and from a practical perspective, to protect the compositions from moisture and premature polymerization. Previous sterilization methods involved either the use of ionizing radiation, including e-beam and gamma ray irradiation, dry heat at elevated temperatures (160° C.), or chemical sterilization such as with ethylene oxide.

When an adhesive composition is applied to a surface to be closed or protected, it is usually in its monomeric form, and the resultant polymerization produces the desired adhesive bond. However, at ordinary temperatures, the monomeric form of the adhesive has a low viscosity which results in the adhesive spreading into undesired areas. Therefore, it is desirable to increase the viscosity of the composition to prevent this unwanted flow. In order to achieve an increased viscosity, thickening agents can be added to the monomeric composition.

The previous methods of sterilization are undesirable in that the high temperatures required for the previous dry heat sterilization processes or irradiation could cause premature polymerization of the monomers. In addition, many polymers that could be used as thickeners underwent degradation resulting in loss of viscosity when exposed to typical dry heat conditions of 160° C. This significantly limits the formulators ability to formulate adhesive compositions which have the desirable stability and flow characteristics, and which can be sterilized.

BRIEF SUMMARY OF THE INVENTION

The present invention is directed to a method of sterilizing 2-cyanoacrylate compositions, including heating the composition in a device at a temperature of from about 70° C. to about 140° C. for an effective amount of time. In another aspect, the invention includes sterilized 2-cyanoacrylate ester compositions for use in medicine or surgery, the compositions being disposed in sealed aluminum containers and being sterilized at a temperature of between about 70° C. and about 140° C. The compositions can be disposed in sealed aluminum, tin, stainless steel tubes or pouches or glass containers. In yet another aspect, the invention is directed to a method for assaying the sterilization of cyanoacrylate compositions.

DETAILED DESCRIPTION OF THE INVENTION

As embodied and described herein, the present invention provides a novel method of sterilizing 2 cyanoacrylate ester compositions using a combination of chemical and heating means, and the resulting novel compositions. The combination of monomeric 2-cyanoacrylate, heat and time have a lethal effect on microbials, rendering sterilized compositions when the appropriate sterilization condition is achieved and when the method is applied to 2-cyanoacrylates in sealed containers.

As used herein, the following terms have the following meanings:

The term "cyanoacrylate adhesive composition" or "cyanoacrylate adhesive compositions" refers to polymerizable formulations comprising polymerizable cyanoacrylate ester monomers. The term aldose is intended to refer to both common disaccharides and monosaccharides.

In the method of the invention, 2-cyanoacrylate adhesive compositions are sterilized through an unexpected and heretofore unknown combination of heat and time, sterilizing at temperatures significantly lower than previously thought to be effective. Previous dry heat sterilization methods have required temperatures of at least 160° C. to 180° C. Heating times at these temperatures were from 2 hours at 160° C. to 30 minutes at 180° C. Under the present invention, the 2-cyanoacrylate adhesive compositions can be sterilized at temperatures from about 70° C. to about 140° C. As would be expected, the time required to effect sterilization will vary depending on the temperature selected to accomplish the sterilization. At 140° C., sterilization requires approximately 30 minutes. At 70° C., sterilization requires about 600 minutes. Required heating times for intermediate temperatures are reported in Tables 2 and 3. Ultimately sterilization times for any composition can be readily determined by one skilled in the art by standard test methods without undue experimentation.

Typical sterilization times are listed in Table 1.

TABLE #1

| sterilization heating times | |
|---|---|
| 70° C. | 600 minutes |
| 80° C. | 480 minutes |
| 90° C. | 300 minutes |
| 100° C. | 120 minutes |
| 110° C. | 90 minutes |
| 120° C. | 60 minutes |
| 130° C. | 60 minutes |
| 140° C. | 30 minutes |

According to the assay method of the invention, sterilization of cyanoacrylate compositions can be assayed for the effectiveness of a given temperature and sterilization time. Samples containing formulated n-butyl cyanoacrylate and 2-octyl cyanoacrylate in sealed borosilicate glass and aluminum tubes were inoculated with *Bacillus subtilis* lyophilized spores at a concentration of $1\times10^{+6}$ per ml of formulation. In other embodiments, spores can be introduced into the cyanoacrylate adhesive compositions prior to sterilization using commercially available biological indicators or spore test strips. Among the commercially available biological indicators which may be used are: bacterial spores on a stainless steel disc, bacterial spores on a steel wire, bacterial spores on steel coupons, bacterial spores on borosilicate paper and bacterial spores on woven cotton threads. Among the species of spores which may be chosen for use in the commercially available biological indicators are *Bacillus subtilis* and *Geobacillus stearothermophilus*. Commercially available biological indicators may be obtained from any commercial supplier, such as Raven Labs. Some inoculated glass vials and tubes samples were kept at room temperature without sterilization as positive controls, while the rest of the samples were sterilized at temperatures ranging from 70 to 140° C. with different time exposures. Samples were sent to a microbiology laboratory for determination of the presence or absence of growth after the sterilization procedure was completed to assay the effectiveness of the process conditions.

In accordance with the present invention it is preferred to utilize microorganisms which may be killed by the sterilization process but which show significant resistance to this process. The term microorganism refers to bacteria, fungi, yeast, protozoa algae, viruses and protozoa. Bacterial spores are very resistant to heat and chemicals; more so than vegetative bacterial cells, therefore the spores are often used to monitor sterilization procedures. A preferred organism for monitoring dry heat sterilization is *Bacillus subtilis*.

The spores represent a resting stage in the life cycle of the *Bacillus* genus. The resting spore contains a large number of active enzymes which allow the transformation from dormant cell to vegetative cell. The germination process, or the return to the vegetative state, has been described as a time-ordered sequence involving activation, triggering, initiation and outgrowth. Activation is reversible and involves an increase in the rate and extent of germination. Triggering is irreversible and is the result of spore contact with the germinant. Initiation involves the loss of heat resistance, release of dipicolinic acid and calcium, loss of refractility and absorbance. Outgrowth results in formation of the vegetative cell.

In accordance with the present invention a cyanoacrylate composition test sample comprising at least one sterility test strip, or lyophilized spores is utilized. While reference is made to "spores" as a test microorganism it should be understood that microorganisms other than spore formers may be used in conjunction with the present invention. The spore strips utilized with the present invention are preferably constructed of materials which are inert to the microorganisms and inert to cyanoacrylate monomer. A variety of commercial spore strips is readily available and can be utilized with the present invention. The spore strips can contain more than one type of microorganism.

To assay the sterilized samples and controls, the compositions including the biological indicators are transferred into containers filled with an aqueous aldose solution, shaken, and transferred into a quantity of nutrient medium in an aseptic container. Transferring the samples to an aldose solution serves to emulsify the cyanoacrylate monomer without causing it to polymerize as it would upon exposure to water alone. Aldoses which act to emulsify the cyanoacrylate include without limitation, dextrose, lactose, arabinose, mannose, galactose, rhamnose, fructose, sucrose and glucose. In one embodiment of the invention, the aldose is dextrose. The concentration of the aldose solution may be from about 2% to about 50% on a weight/weight basis. A preferred range for the concentration of the aldose solution is from about 3% to about 15%. A more preferred aldose concentration is from about 5% to about 10% weight/weight. The nutrient medium supports the germination of spores and growth of any viable microorganisms. The nutrient medium contains a protein substrate for the proteases liberated during spore germination and during subsequent microbial growth. The nutrient medium preferably comprises an aqueous solution or suspension of nutrient components (including the protein substrate) needed in order to promote the growth of viable microorganisms that may exist after the sterilization process. One example of a suitable culture medium is a protein-containing microbiological broth such as tryptic soy broth (TSB) and/or TSB with specific protein additives, such as, for example, casein. Formulations for culture media are well-known to those in the art.

The mixture of microorganisms, cyanoacrylate, aldose and nutrient medium are then sealed within a containing means. The samples are then incubated for a predetermined period of time at from about 28° C. to about 37° C. Any microorganisms not killed during the sterilization process begin to germinate and grow during the incubation period. In a preferred embodiment the microorganisms are incubated for at least about seven days. Thereafter the sample is examined to detect the presence of growth by different methods, such as visual examination of the samples followed by microscope Gram stain examination, addition of an enzymatic indicator such as tetrazolium salts followed by UV spectrophotometric analysis, or direct UV spectrophotometric analysis of incubated samples. In one embodiment, after visual examination a gram stain smear is prepared to look for gram positive rods which would confirm growth. In another embodiment, growth can be determined by the addition of enzymatic biological indicator such as tetrazolium salts, wherein bacterial activity is determined by development of color which may be measured quantitatively with an ultraviolet spectrophotometer at 257 nm. In yet another embodiment, a sample without enzymatic indicator is analyzed under a spectrophotometer at a wavelength of 480 nm to determine growth.

The method of the invention can be applied in principle to any 2-cyanoacrylate ester monomer. The 2-cyanoacrylate is preferably an aliphatic cyanoacrylate ester and preferably an alkyl, cycloalkyl, alkenyl, alkoxyalkyl, fluoroalkyl, fluorocyclic alkyl or fluoroalkoxy 2-cyanoacrylate ester. The alkyl group may contain from 2 to 12 carbon atoms, and is preferably a $C_2$ to $C_8$ alkyl ester, and is most preferably a $C_4$ to $C_9$ alkyl ester. Suitable 2-cyanoacrylate esters include without limitation, the ethyl, n-propyl, iso-propyl, n-butyl, pentyl, hexyl, cyclohexyl, heptyl, n-octyl, 2-ethylhexyl, 2-methoxyethyl and 2-ethoxyethyl esters. Any of these 2-cyanoacrylate monomers may be used alone, or they may be used in mixtures.

The 2-cyanoacrylate monomers of the invention can be prepared by any of the methods known in the art. U.S. Pat. Nos. 2,721,858, 3,254,111 and 4,364,876, each of which is hereby incorporated in its entirety by reference, disclose methods for preparing 2-cyanoacrylates. For example, cyanoacrylates for the instant invention were prepared by reacting cyanoacetate with formaldehyde in the presence of heat and a basic condensation catalyst to give a low molecular weight polymer. A depolymerization step followed under heat and vacuum in the presence of acidic and anionic inhibitors, yielding a crude monomer that could be distilled under vacuum and in the presence of radical and acidic inhibitors. The distilled 2-cyanoacrylate monomers are then formulated with radical and acidic inhibitors depending upon their application and to provide the necessary stability.

The 2-cyanoacrylate compositions of the invention may in some embodiments contain a thickening agent to increase the viscosity of the composition. This thickening agent may be a polymer. The thickening agent may be selected from the group consisting of without limitation, poly alkyl 2-cyanoacrylates, poly cycloalkyl-2-cyanoacrylates, poly fluoroalkyl-2-cyanoacrylates, poly fluorocycloalkyl-2-cyanoacrylates, poly alkoxyalkyl-2-cyanoacrylates, poly alkoxycycloalkyl-2-cyanoacrylates, poly fluoroalkoxyalkyl-2-cyanoacrylates, polyalkoxycyclofluoroalkyl-2-cyanoacrylates, poly vinylacetate, poly lactic acid and poly glycolic acid. In order to obtain optimum solubility of the polymer in the monomer, the polymer is often chosen to be a polymer of the monomer or one of the monomers which comprise the 2-cyanoacrylate composition. Preferably, the polymer is soluble in the monomer composition at ambient temperature. Preferred polymers include polymers of octyl 2-cyanoacrylate, vinyl acetate lactic acid, or glycolic acid. The preferred weight average molecular weight of the polymers is from about 300,000 to about 2,000,000. More preferably, the polymer molecular weight is from about 500,000 to about 1,600,000.

Cyanoacrylate polymers of the invention can be prepared by slow addition of the monomer to a mixer containing 0.1% bicarbonate deionized water. Water is then decanted away, and the polymer is rinsed several times with deionized water and decanted again. Following steps include neutralizing the polymer with 0.1 N HCl, rinsing with deionized water, drying on a vacuum heated oven at temperature of less than 80° C. and grinding the polymer to fine particles.

The amount of thickening agent that is added to the monomer composition is dependent upon the molecular weight of the polymer and the desired viscosity for the adhesive composition. The thickening agent typically is added at from about 1% to about 25% by weight of the composition. Preferably it is added at from about 1% to about 10%. More preferably it is added at from about 1% to about 5%. A typical viscosity of the composition is from about 25 to about 3000 centipoise, as measured by a Brookfield viscometer at 25° C. Preferably, the viscosity is between from about 50 to 600 centipoise at 25° C. The specific amount of a given thickening agent to be added can be determined by one of ordinary skill in the art without undue experimentation.

The 2-cyanoacrylate compositions may contain one or more acidic inhibitors in the range from 1 to 1,000 ppm. Such acidic inhibitors include without limitation: sulfur dioxide, nitrogen oxide, boron oxide, phosphoric acid, ortho, meta, or para-phosphoric acid, acetic acid, benzoic acid, cyanoacetic acid, tri-fluoroacetic acid, tribromoacetic acid, trichloroacetic acid, boron trifluoride, hydrogen fluoride, perchloric acid, hydrochloric acid, hydrobromic acid, sulfonic acid, fluorosulfonic acid, chlorosulfonic acid, sulfuric acid, and toluenesulfonic acid.

The 2-cyanoacrylate compositions may contain one or more free radical polymerization inhibitors in the range from 0 to 10,000 ppm. Examples such radical inhibitors include, without limitation, catechol, hydroquinone, hydroquinone monomethyl ether and hindered phenols such as butylated hydroxyanisol, butylated hydroxytoluene (2,6-di-tert-butyl butylphenol and 4-methoxyphenol), 4-ethoxyphenol, 3 methoxyphenol, 2-tert-butyl-4-methoxyphenol and 2,2 methylene-bis-(4-methyl-6-tert-butylphenol).

The 2-cyanoacrylate compositions may contain single or mixtures of plasticizers such as tributyl acetyl citrate, dimethyl sebacata, diethyl sebacate, try-ethyl phosphate, tri-(2-ethylhexyl)phosphate, tri-cresyl phosphate, glyceryl tri acetate, glyceryl tributyrate, dioctyl adipate, isopropyl myristate, butyl stearate, trioctyl trimellitate, and dioctyl glutarate. The plasticizers may be added to the compositions in proportions of less than 50% w/w of the formulation.

The 2-cyanoacrylate compositions may contain small amounts of dyes like the derivatives of anthracene and other complex structures. Some of these dyes include, without limitation, 1-hydroxy-4-[4-methylphenylamino]-9,10 anthracenedione (D&C violet No. 2), disodium salt of 6-hydroxy-5-[(4-sulfophenyl)axo]-2-naphthalene-sulfonic acid (FD&C Yellow No. 6,) 9-(o-carboxyphenyl)-6-hydroxy-2,4,5,7-tetraiodo-3H-xanthen-3-one disodium salt monohydrate (FD&C Red No. 3), 2-(1,3-dihydro-3-oxo-5-sulfo-2-indole-2-ylidine)-2,3-dihydro-3-oxo-1H-indole-5-sulfonic acid disodium salt (FD&C Blue No. 2), and [phthalocyaninato (2)]copper added in proportions of less than 50,000 ppm.

The sterilized cyanoacrylate adhesive compositions of the invention may be packaged in a container made of any suitable material. Suitable materials must be heat stable and resistant up to the sterilization temperature, must provide an adequate barrier to atmospheric moisture and be compatible with the cyanoacrylate monomer or monomers. Materials meeting these requirements include metals and borosilicate type I glass. Suitable metals can include without limitation aluminum, tin, and stainless steel. Metals can have different forms like pouches and tubes. Glass can be used as vials, breakable tubes or any other shape, and contained inside tubes made out of the same material, or combinations or materials including plastics. Particularly preferred materials are aluminum and type 1 glass. Preferred aluminum tubes comprise a nozzle which is hermetically sealed by a pierceable membrane of aluminum and are filled at their end remote from the nozzle prior to closure of the open end by tight crimping. The glass vials used in this invention, are made out of borosilicate type I glass and sealed with a threaded phenolic cap with a silicone/Teflon septum or sealed with an aluminum crimp cap and a silicon/Teflon septum. In the result, therefore, preferred embodiments of the invention reside in a substantially hermetically sealed aluminum container, e.g. an aluminum tube, containing a sterile 2-cyanoacrylate composition or type I glass vials hermetically sealed with a phenolic threaded cap and a silicone/Teflon septum.

EXAMPLES

Example 1

Sample Testing: Sterility Test Method for all Samples

The method was tested by first performing the USP bacteriostasis and fungi stasis test on glass vials and aluminum tubes. The sterility test was performed by obtaining spores of *Bacillus subtilis* var. *niger* suspended in irrigation water at a concentration of $2.3 \times 10^{+8}$/ml. Aliquots of 0.48 ml of these spores were placed in glass serum bottles, lyophilized and then reconstituted with 50 ml of n-butyl or 2-octylcyanoacrylate compositions to obtain a volume of 50 ml of inoculated spore solution with a concentration $2 \times 10^{+6}$/ml. These cyanoacrylate spore solutions were used to fill the tubes and vials for the sterilization trials at different temperatures and time and for the non-sterilized (standard biological indicators) control vials and tubes. Each tube and vial was filled with a volume of 0.5 to 0.6 ml of a cyanoacrylate composition that rendered a spore concentration of $2 \times 10^{+6}$/ml. Non-sterilized biological indicators and sterilized spores inoculated samples at different temperatures and time were transferred to a 5% dextrose USP solution, shaken and transferred to soy casein digested broth (SCDB) and incubated at 35-37° C. for at least seven days. A vial of lyophilized spores with no cyanoacrylate was tested for population verification. The vial was transferred to sterile purified water and vortexed for 10 minutes. Serial dilutions of $10^{+4}$, $10^{-5}$, and $10^{+6}$ were plated in duplicate using soy casein digested broth (SCDB) and incubated for 48 hours at 35-37° C. The $10^{+6}$ dilution yielded duplicate plates in the countable range. The final calculations showed there were $6.1 \times 10^{+6}$ CFU/ml, or $3.1 \times 10^{+7}$ CFU/vial.

Polymer Preparation: (Polymer Method for Samples Containing Polymer)

2-OCA polymer was made by adding drop by drop 30 grams of 2-OCA monomer to a blender containing 1000 ml of 0.1% bicarbonate deionized water while swirling. Bicarbonate water with the polymer was vacuum filtered on a Kitasato with a Fisherbrand #Q5 quantitative filter paper, rinsed five times with 500 ml aliquots of deionized water and decanted. The polymer was neutralized with 500 ml of 0.1 N hydrochloric acid. The neutralized polymer was rinsed with three aliquots of 500 ml, decanted, dried in a vacuum oven at 80° C., and after drying was finely ground with a mixer.

Sample Composition Preparation:

The sample of 2-OCA containing polymer was made by mixing 2-octyl cyanoacrylate (stabilized with 100 ppm of $SO_2$, 1000 ppm of butylated hydroxyanisole) with 3.5% of 2-OCA polymer. The polymer was dissolved in the formulated 2-OCA by heating and mixing in a round glass flask equipped with a paddle shaft and mixer at a temperature no higher than 80° C. and obtaining a viscosity of 567 cp (measured with a Brookfield DV-II at 25° C.). Then, the composition was inoculated with lyophilized *Bacillus subtilis* spores to produce a minimum concentration of $1\times10^{-6}$ which were filled in aluminum tubes and glass type I glass threaded vials. Tubes were sealed by crimping with a Kentex automatic tubes filler and sealer. The glass vials were filled with an Eppendorf automatic pipette and sealed with threaded phenol caps and silicone/Teflon septa. Some inoculated glass and tube samples were not sterilized and were used as positive standard biological indicators to indicate livable spores. The rest of the inoculated and sealed tubes and vials were exposed to the experimental temperatures and time stipulated in the sterilization testing protocol conditions.

Tables #2-3 shows example results.

TABLE #2

2-OCA sterilization example packed in glass vials with pre-sterilization viscosity of 567 cp

| Sterilization °C. | Sterilization time minutes | Type of media 400 ml | Incubation temperature °C. | Number samples tested | Number of days incubated | Number of positives | Viscosity @ 25° C. sterile |
|---|---|---|---|---|---|---|---|
| 90 | 240 | SCDB | 30-35 | 3 | 7 | 1 | 566 |
| 100 | 120 | SCDB | 30-35 | 3 | 7 | 0 | 569 |
| 100 | 180 | SCDB | 30-35 | 3 | 7 | 0 | 562 |
| 110 | 60 | SCDB | 30-35 | 3 | 7 | 0 | 526 |
| 110 | 120 | SCDB | 30-35 | 3 | 7 | 0 | 452 |
| 120 | 60 | SCDB | 30-35 | 3 | 7 | 0 | 418 |
| 120 | 90 | SCDB | 30-35 | 3 | 7 | 0 | N/A |
| 130 | 60 | SCDB | 30-35 | 3 | 7 | 0 | 343 |
| 130 | 120 | SCDB | 30-35 | 3 | 7 | 0 | N/A |
| 140 | 30 | SCDB | 30-35 | 3 | 7 | 0 | 110 |
| 140 | 45 | SCDB | 30-35 | 3 | 7 | 0 | N/A |

Table #2 above shows minimum sterilization temperatures, incubation temperature, incubation time and the results obtained for samples of *Bacillus subtilis* spores inoculated 2-OCA containing 3.5% 2-OCA polymer (567 cp), 100 ppm $SO_2$ and 1000 ppm BHA.

Table #3 above shows minimum sterilization temperatures, incubation temperature, incubation time and the results obtained for samples of *Bacillus subtilis* spores inoculated 2-OCA containing 3.5% 2-OCA polymer (567 cp), 100 ppm $SO_2$ and 1000 ppm BHA. Note the sharp drop in the viscosities of the compositions tested and shown in Tables 2 and 3 as temperature passes 110° C. The average viscosity drop from the base viscosity (567 cp) in the last column in each table going from row 4 to row 5 is 14.45%.

Example II

Sample Composition Preparation:

Sample IIA:

A sample of n-butyl cyanoacrylate (n-BCA) with a viscosity of 2.8 cp (measured with a Brookfield DV-II at 25° C.) containing 100 ppm of $SO_2$ and 1000 ppm of butylated hydroxyanisole (BHA) was prepared for this example. Then, the composition was inoculated with biological indicator standards such as borosilicate spore discs, cotton threads and spore wires with a spore concentration of $1\times10^{+6}$ *Geobacillus stearothermophilus*. The spore inoculated composition was filled in type I glass threaded vials with an Eppendorf automatic pipette and sealed with threaded phenol caps and silicone/Teflon septa. Some inoculated glass vials were not sterilized and were used as positive standard biological indicators to indicate livable spores. The rest of the inoculated sealed

TABLE #3

2-OCA sterilization example packed in aluminum tubes with pre-sterilization viscosity of 567 cp

| Sterilization °C. | Sterilization time minutes | Type of media 400 ml | Incubation temperature °C. | Number samples tested | Number of days incubated | Number of positives | Viscosity @ 25° C. sterile |
|---|---|---|---|---|---|---|---|
| 90 | 240 | SCDB | 30-35 | 3 | 7 | 2 | 565 |
| 100 | 120 | SCDB | 30-35 | 3 | 7 | 0 | 566 |
| 100 | 180 | SCDB | 30-35 | 3 | 7 | 0 | 570 |
| 110 | 60 | SCDB | 30-35 | 3 | 7 | 0 | 526 |
| 110 | 120 | SCDB | 30-35 | 3 | 7 | 0 | 435 |
| 120 | 60 | SCDB | 30-35 | 3 | 7 | 0 | 405 |
| 120 | 90 | SCDB | 30-35 | 3 | 7 | 0 | N/A |
| 130 | 60 | SCDB | 30-35 | 3 | 7 | 0 | 351 |
| 130 | 120 | SCDB | 30-35 | 3 | 7 | 0 | N/A |
| 140 | 30 | SCDB | 30-35 | 3 | 7 | 0 | 102 |
| 140 | 45 | SCDB | 30-35 | 3 | 7 | 0 | N/A | vials were exposed to the experimental temperatures and times stipulated in the sterilization testing protocol conditions.
Table #4 shows example results.

TABLE #4 n-BCA monomer sterilization example in glass vials with pre-sterilization viscosity of 2.8 cp

| Sterilization 100° C. | Sterilization time minutes | Type of media 400 ml | Incubation temperature ° C. | Number samples tested | Number of days incubated | Number of positives | Viscosity @ 25° C. sterile |
|---|---|---|---|---|---|---|---|
| Borosilicate disc | 240 | SCDB | 55-60 | 3 | 7 | 0 | 2.9 |
| Cotton threads | 240 | SCDB | 55-60 | 3 | 7 | 0 | 2.8 |
| SS wires | 240 | SCDB | 55-60 | 3 | 7 | 0 | 2.8 |
| Positive control borosilicate disc | NO | SCDB | 55-60 | 3 | 2 | 3 | 2.8 |
| Positive Control cotton threads | NO | SCDB | 55-60 | 3 | 2 | 3 | 2.9 |
| SS wires | NO | SCDB | 55-60 | 3 | 2 | 3 | 2.8 |

Table #4 above shows sterilization temperatures, incubation temperature, incubation time and the results obtained for samples of *Geobacillus stearothermophilus* spores inoculated n-BCA containing, 100 ppm $SO_2$ and 1000 ppm BHA.
Sample IIB:

A sample of n-butyl cyanoacrylate (n-BCA) with a viscosity of 2.8 cp (measured with a Brookfield DV-II at 25° C.) containing 100 ppm of $SO_2$ and 1000 ppm of butylated hydroxyanisole (BHA) was prepared for this example. Then, the composition was inoculated with biological indicator standards cotton threads with a spore concentration of $1 \times 10^{+6}$ *Bacillus subtilis*. The spore inoculated composition was filled in type 1 glass threaded vials with an Eppendorf automatic pipette and sealed with threaded phenol caps and silicone/Teflon septa. Some inoculated glass vials were not sterilized and were used as positive standard biological indicators to indicate livable spores. The rest of the inoculated sealed vials were exposed to the experimental temperatures and times stipulated in the sterilization testing protocol conditions.
Tables #5 shows example results.

Table #5 above shows sterilization temperatures, incubation temperature, incubation time and the results obtained for samples of *Bacillus subtilis* spores inoculated n-BCA containing 100 ppm $SO_2$ and 1000 ppm BHA.

The invention claimed is:

1. A method of sterilization of a 2-cyanoacrylate adhesive composition comprising the steps of:
    (a) placing in a container comprised of type I glass at least one 2-cyanoacrylate monomer with at least one polymeric thickener homologous to at least one of the monomers, establishing an initial viscosity that will not increase when the composition is sterilized at a temperature no greater than approximately 110° C.:
    (b) sealing the container; and
    (c) heating the composition in the container at a temperature of no greater than approximately 110° C. for a period of time sufficient to sterilize the composition.

2. The method of claim 1, further comprising, between said steps (a) and (b), the additional steps of:
    (a)(1) dissolving approximately 100 to 1000 ppm by weight of $SO_2$ and approximately 100 to 10,000 ppm by weight of butylated hydroxyanisole (BHA) in the composition; and
    (a)(2) dissolving up to approximately 50% by weight of plasticizer in the resulting liquid.

TABLE #5 n-BCA monomer sterilization example in glass vials with pre-sterilization viscosity of 2.8 cp

| Sterilization 100° C. | Sterilization time minutes | Type of media 400 ml | Incubation temperature ° C. | Number samples tested | Number of days incubated | Number of positives | Viscosity @ 25° C. sterile |
|---|---|---|---|---|---|---|---|
| Cotton threads | 240 | SCDB | 55-60 | 3 | 7 | 1 | 2.8 |
| Positive Control cotton threads | NO | SCDB | 55-60 | 3 | 2 | 3 | 2.8 |

3. The method of claim 1, in which:
said initial viscosity is in the range of about 400 to about 600 centipoises.

4. A method as in claim 1, wherein:
said 2-cyanoacrylate adhesive composition comprises one or more 2-cyanoacrylate ester monomers wherein said cyanoacrylate ester monomer is an alkyl, cycloalkyl, fluoroalkyl, fluorocycloalkyl or fluoroalkoxy 2-cyanoacrylate monomer.

5. A method according to claim 1, wherein:
said 2-cyanoacrylate adhesive composition further comprises one or more 2-cyanoacrylate ester monomers including octyl-2-cyanoacrylate monomer.

6. A method according to claim 1, wherein:
said at least one polymeric thickener is a poly alkyl-2-cyanoacrylate.

7. A method according to claim 6, wherein:
the alkyl group of the poly alkyl-2-cyanoacrylate is selected from the group consisting of straight chain or branched chain $C_4$ to $C_8$ hydrocarbons.

8. A method according to claim 7, wherein:
said alkyl group is an octyl group.

9. A method according to claim 1, wherein:
said 2-cyanoacrylate adhesive composition further comprises a stabilizer.

10. A method according to claim 9, wherein:
said stabilizer comprises at least one anionic polymerization inhibitor and at least one free radical polymerization inhibitor.

11. A method according to claim 1, wherein:
said composition comprises a plasticizer selected from the group consisting of tributyl acetyl citrate, dimethyl sebacate, diethyl sebacate, triethyl phosphate, tri-(2-ethylhexyl) phosphate, tricresyl phosphate, glycerol triacetate, glycerol tributyrate, dioctyl adipate, isopropyl myristate, butyl stearate, trioctyl trimellitate and dioctyl glutarate.

12. A method of sterilization of 2-cyanoacrylate adhesive compositions, comprising the steps of:
  (a) providing a container comprised of type I glass;
  (b) placing in the container at least one 2-cyanoacrylate monomer with at least one polymeric thickener homologous to at least one of the monomers to establish an initial viscosity that will not increase when the composition is sterilized at a temperature no greater than approximately 110° C.;
  (c) dissolving up to approximately 50% by weight of plasticizer in the resulting composition;
  (d) sealing the container; and
  (e) heating said composition in the container at a temperature of no greater than approximately 110° C. for a period of time sufficient to sterilize the composition.

13. A method as in claim 12, wherein:
said cyanoacrylate composition comprises one or more 2-cyanoacrylate ester monomers wherein said cyanoacrylate ester monomer is an alkyl, cycloalkyl, fluoroalkyl, fluorocycloalkyl or fluoroalkoxy 2-cyanoacrylate monomer.

14. A method according to claim 13, wherein:
the 2-cyanoacrylate composition further comprises a stabilizer.

15. A method according to claim 14, wherein:
said stabilizer comprises at least one anionic polymerization inhibitor and at least one free radical polymerization inhibitor.

16. A method according to claim 13, wherein:
said cyanoacrylate composition further comprises a plasticizer selected from the group consisting of tributyl acetyl citrate, dimethyl sebacate, diethyl sebacate, triethyl phosphate, tri-(2-ethylhexyl) phosphate, tricresyl phosphate, glycerol triacetate, glycerol tributyrate, dioctyl adipate, isopropyl myristate, butyl stearate, trioctyl trimellitate and dioctyl glutarate.

17. A method according to claim 12, wherein:
a thickener is a poly alkyl-2-cyanoacrylate.

18. A method according to claim 17, wherein:
the alkyl group of the poly alkyl-2-cyanoacrylate is selected from the group consisting of straight chain or branched chain $C_4$ to $C_8$ hydrocarbons.

19. A method according to claim 17, wherein:
said thickener is poly octyl-2-cyanoacrylate.

20. The method of claim 12, in which:
said initial viscosity is in the range of about 400 to about 600 centipoises.

21. The method of claim 12, further comprising, between said steps (b) and (c), the additional steps of:
  (b)(1) dissolving approximately 100 to 1000 ppm by weight of $SO_2$ and approximately 100 to 10,000 ppm by weight of butylated hydroxyanisole (BHA) in the composition; and
  (b)(2) dissolving up to approximately 50% by weight of plasticizer in the resulting liquid.

22. An article of manufacture, comprising:
a type I glass vial packed with a mixture of about 3.5% by weight of polyoctyl-2-cyanoacrylate, about 100 ppm $SO_2$, and about 1000 ppm butylated hydroxyanisole (BHA), all dissolved in the balance percentage by weight of octyl-2-cyanoacrylate monomer, then sealed; and
the sealed vial heated to a temperature of between about 100° C. and about 110° C. for a period of time between about 60 minutes and 180 minutes, establishing a sterile adhesive having a viscosity of between about 430 centipoises and about 570 centipoises.

* * * * *